United States Patent
Ozasa et al.

(10) Patent No.: US 11,291,798 B2
(45) Date of Patent: Apr. 5, 2022

(54) VASCULAR EMBOLIZATION DEVICE AND PRODUCTION METHOD THEREFOR

(71) Applicant: KANEKA MEDIX CORPORATION, Osaka (JP)

(72) Inventors: Hitoshi Ozasa, Settsu (JP); Atsushi Ogawa, Tokyo (JP); Yasushi Yamanaka, Settsu (JP); Hiroo Iwata, Mishima-gun (JP); Tomonobu Kodama, Tokyo (JP)

(73) Assignee: KANEKA MEDIX CORPORATION, Osaka (JP)

( * ) Notice: Subject to any disclaimer, the term of this patent is extended or adjusted under 35 U.S.C. 154(b) by 114 days.

(21) Appl. No.: 15/555,458

(22) PCT Filed: Mar. 3, 2016

(86) PCT No.: PCT/JP2016/056617
§ 371 (c)(1),
(2) Date: Sep. 1, 2017

(87) PCT Pub. No.: WO2016/140313
PCT Pub. Date: Sep. 9, 2016

(65) Prior Publication Data
US 2018/0036508 A1 Feb. 8, 2018

(30) Foreign Application Priority Data
Mar. 3, 2015 (JP) .............................. JP2015-041624

(51) Int. Cl.
*A61M 25/00* (2006.01)
*A61L 31/16* (2006.01)
(Continued)

(52) U.S. Cl.
CPC .......... *A61M 25/0045* (2013.01); *A61B 5/02* (2013.01); *A61B 17/12022* (2013.01);
(Continued)

(58) Field of Classification Search
CPC .......... A61B 17/1214; A61B 17/12145; A61B 17/1215; A61B 17/12154;
(Continued)

(56) References Cited

U.S. PATENT DOCUMENTS 4,739,768 A 4/1988 Engelson
4,884,579 A 12/1989 Engelson
(Continued)

FOREIGN PATENT DOCUMENTS

JP 5-500322 A 1/1993
JP 7-502674 A 3/1995
(Continued)

OTHER PUBLICATIONS

Applicant brings to the attention of the Examiner the existence of copending U.S. Appl. No. 15/555,449 by the same Inventor (Hitoshi Ozasa)/Applicant (Kaneka Medix Corporation) as the present case, filed Sep. 1, 2017, and published as US 2018/0028190 A1 on Feb. 1, 2018, and which is the national stage of PCT/JP2016/056618, which was filed on Mar. 3, 2016, and was published as WO 2016/140314 A1 on Sep. 9, 2016.
(Continued)

*Primary Examiner* — Ashley L Fishback
(74) *Attorney, Agent, or Firm* — Birch, Stewart, Kolasch & Birch, LLP

(57) ABSTRACT

A vascular embolization device includes a coil with a primary shape and an stretch resistant wire provided inside the coil, in which the stretch resistant wire is a multilayer strand including at least one core layer and at least one outer layer including one or more resin compositions and a biochemical active material, and the core layer is composed of a material with a tensile break strength higher than that of
(Continued)

the outer layer. The vascular embolization device has the function of administering a biochemical active material and also has good flexibility.

16 Claims, 8 Drawing Sheets

(51) Int. Cl.
  *A61B 5/02* (2006.01)
  *A61B 17/12* (2006.01)
  *A61L 29/08* (2006.01)
  *A61L 31/10* (2006.01)
  *A61M 25/01* (2006.01)
  *A61B 17/00* (2006.01)
  *A61M 25/09* (2006.01)

(52) U.S. Cl.
  CPC .. *A61B 17/12145* (2013.01); *A61B 17/12154* (2013.01); *A61L 29/085* (2013.01); *A61L 31/10* (2013.01); *A61L 31/16* (2013.01); *A61M 25/01* (2013.01); *A61B 17/12113* (2013.01); *A61B 2017/00004* (2013.01); *A61B 2017/00526* (2013.01); *A61B 2017/00871* (2013.01); *A61B 2017/00893* (2013.01); *A61B 2017/1205* (2013.01); *A61B 2017/12063* (2013.01); *A61B 2017/12068* (2013.01); *A61L 2300/434* (2013.01); *A61L 2430/36* (2013.01); *A61M 2025/0047* (2013.01); *A61M 2025/0915* (2013.01); *A61M 2025/09175* (2013.01)

(58) Field of Classification Search
  CPC ........ A61B 17/12163; A61B 17/12168; A61B 17/12172; A61B 17/12177; A61B 17/06166; A61B 2017/06176; A61B 2017/0618; A61B 2017/06185; A61B 2017/0619
  See application file for complete search history.

(56) References Cited

U.S. PATENT DOCUMENTS

| | | |
|---|---|---|
| 6,280,457 B1 | 8/2001 | Wallace et al. |
| 2005/0090856 A1 | 4/2005 | Porter |
| 2005/0149109 A1* | 7/2005 | Wallace ........... A61B 17/12022 606/200 |
| 2006/0173488 A1 | 8/2006 | Takeuchi et al. |
| 2006/0217758 A1 | 9/2006 | Ogawa et al. |
| 2007/0232169 A1* | 10/2007 | Strickler ................. A61L 27/26 442/181 |
| 2007/0299461 A1* | 12/2007 | Elliott ................ A61B 17/1214 606/191 |
| 2008/0228215 A1* | 9/2008 | Strauss ............ A61B 17/12022 606/191 |
| 2009/0187206 A1* | 7/2009 | Binmoeller ........... A61F 5/0013 606/191 |
| 2011/0118772 A1 | 5/2011 | Chen et al. |
| 2011/0313443 A1* | 12/2011 | Lorenzo ........... A61B 17/12022 606/200 |
| 2012/0172921 A1* | 7/2012 | Yamanaka ....... A61B 17/12022 606/200 |
| 2012/0253381 A1* | 10/2012 | Forsythe ............ A61B 17/1215 606/200 |
| 2013/0131711 A1 | 5/2013 | Bowman |
| 2013/0178892 A1 | 7/2013 | Iwata et al. |
| 2018/0028190 A1 | 2/2018 | Ozasa et al. |

FOREIGN PATENT DOCUMENTS

| | | |
|---|---|---|
| JP | 8-501015 A | 2/1996 |
| JP | 11-076249 A | 3/1999 |
| JP | 2003-501131 A | 1/2003 |
| JP | 2007-523055 A | 8/2007 |
| JP | 2013-537046 A | 9/2013 |
| JP | 2015-501702 A | 1/2015 |
| WO | WO 91/13592 A1 | 9/1991 |
| WO | WO 94/06503 A1 | 3/1994 |
| WO | WO 95/12367 A1 | 5/1995 |
| WO | WO 2004/062510 A1 | 7/2004 |
| WO | WO 2004/073528 A1 | 9/2004 |

OTHER PUBLICATIONS

International Search Report (PCT/ISA/210) issued in PCT/JP2016/056617, dated May 31, 2016.
Written Opinion (PCT/ISA/237) issued in PCT/JP2016/056617, dated May 31, 2016.

* cited by examiner (a)

(b)

VASCULAR EMBOLIZATION DEVICE AND PRODUCTION METHOD THEREFOR

TECHNICAL FIELD

The present invention relates to a vascular embolization device to be placed at a predetermined site in a blood vessel and to embolize the blood vessel.

BACKGROUND ART

Less invasive therapies widely used to treat, for example, aneurysm include vascular embolization in which an embolization device is placed in the dome (Patent Literatures 1 and 2). In the vascular embolization, the embolization device placed in the aneurysm serves as a physical barrier against blood flow and causes the formation of a thrombus around the embolization device, so that the risk of aneurysm rupture will decrease. A known embolization device to be placed at a predetermined site in a blood vessel, such as aneurysm, includes a metal coil (hereinafter such a device will also be called an "embolization coil") (Patent Literatures 3 to 5). Such an embolization coil is introduced into the aneurysm through an appropriate catheter by pushing means (an introducer), which is detachably connected to an end of the embolization coil.

In some target sites (cases) where the embolization coil is to be placed, however, a biochemical active material needs to be administered to the target sites.

For example, if no biochemical active material is administered, biological tissues may insufficiently form around the embolization coil placed in the aneurysm, so that the blood may enter the aneurysm to cause recanalization, which may enlarge the dome again. Therefore, it is preferable that an organization promoter be administered into the aneurysm to promote the formation of biological tissues around the embolization coil placed in the aneurysm.

Patent Literature 6 describes an embolization device capable of administering a biochemical active material or a drug, which includes a metal coil and a resin wire that is provided over the inside of the metal coil and contains the biochemical active material or the drug.

CITATIONS LIST

Patent Literatures

Patent Literature 1: U.S. Pat. No. 4,884,579
Patent Literature 2: U.S. Pat. No. 4,739,768
Patent Literature 3: Japanese Translation of PCT International Application Publication No. 05-500322
Patent Literature 4: Japanese Translation of PCT International Application Publication No. 08-501015
Patent Literature 5: Japanese Translation of PCT International Application Publication No. 07-502674
Patent Literature 6: Japanese Unexamined Patent Application Publication No. 11-76249

SUMMARY OF INVENTION

Technical Problems

However, the addition of a biochemical active material to a resin wire can cause the resin wire to have insufficient flexibility, which means that there is room for improvement in ease of handling devices to be inserted into blood vessels and to embolize blood vessels.

It is an object of the present invention to provide a vascular embolization device having the function of administering a biochemical active material and having good flexibility.

Solutions to Problems

As a result of intensive studies to solve the above problems, the inventors have accomplished the present invention. Specifically, the present invention provides a vascular embolization device defined by any one of items [1] to [10] below and an embolization device producing method defined by item [11] below.

[1] A vascular embolization device including: a coil with a primary shape; and a stretch resistant wire provided in an inside of the coil, in which the stretch resistant wire is a multilayer strand including at least one core layer and at least one outer layer including one or more resin compositions and a biochemical active material, and the core layer includes a material with a tensile break strength higher than that of the outer layer.

[2] The vascular embolization device according to item [1], which has a structure in which the coil with the primary shape is further wound into a secondary shape.

[3] The vascular embolization device according to item [1] or [2], in which the resin composition includes a biodegradable resin or an ethylene-vinyl acetate copolymer.

[4] The vascular embolization device according to item [3], in which the biodegradable resin has a weight average molecular weight of 1,000 to 200,000.

[5] The vascular embolization device according to item [3], in which the ethylene-vinyl acetate copolymer has a vinyl acetate unit content of 10 to 50% by weight.

[6] The vascular embolization device according to any one of items [1] to [5], in which the stretch resistant wire has a thickness of 0.01 to 0.10 mm.

[7] The vascular embolization device according to any one of items [1] to [6], in which the stretch resistant wire has a breaking strength of 0.05 N or more per wire.

[8] The vascular embolization device according to any one of items [1] to [7], in which the stretch resistant wire is corrugated or spirally shaped.

[9] The vascular embolization device according to any one of items [1] to [8], in which the stretch resistant wire has a natural length at least 5% longer than the natural length of the coil.

[10] The vascular embolization device according to any one of items [1] to [9], in which the core layer of the stretch resistant wire is made of a metal.

[11] The vascular embolization device according to any one of items [1] to [9], in which the core layer of the stretch resistant wire is made of a resin.

[12] The vascular embolization device according to item [10], in which the core layer of the stretch resistant wire is made of the metal selected from the group consisting of gold, platinum, iridium, tungsten, tantalum, titanium, nickel, copper, iron, and an alloy of any combination thereof.

[13] The vascular embolization device according to item [11], in which the core layer of the stretch resistant wire is made of the resin selected from the group consisting of polyethylene, polypropylene, nylon, polyester, polydioxanone, polytetrafluoroethylene, polyglycolic acid, polylactic acid, silk, and a composite material of any combination thereof.

[14] The vascular embolization device according to any one of items [1] to [13], in which the outer layer on the outermost side contains the biochemical active material.

[15] The vascular embolization device according to any one of items [1] to [14], in which the biochemical active material includes a statin.

[16] The vascular embolization device according to item [15], in which the statin is simvastatin, pravastatin, atorvastatin, pitavastatin, or any combination thereof.

[17] A method for producing the vascular embolization device according to any one of items [1] to [16], the method including the three steps of:

(a) coating a surface of the material forming the core layer with a solution containing the biochemical active material and the resin composition;

(b) drying the solution to form the outer layer containing one or more resin compositions, thereby preparing the stretch resistant wire; and (c) inserting the stretch resistant wire into the inside of the coil to form the vascular embolization device.

Advantageous Effects of Invention

The present invention makes it possible to provide a vascular embolization device having the function of administering a desired biochemical active material to target sites, and also having good flexibility so that it can provide a good embolization effect at various target sites in blood vessels.

DESCRIPTION OF EMBODIMENTS

Hereinafter, a vascular embolization device according to an embodiment of the present invention will be described, with reference to the drawings. It will be understood that such an embodiment is not intended to limit the present invention.

(Vascular Embolization Device)

Figure 1:
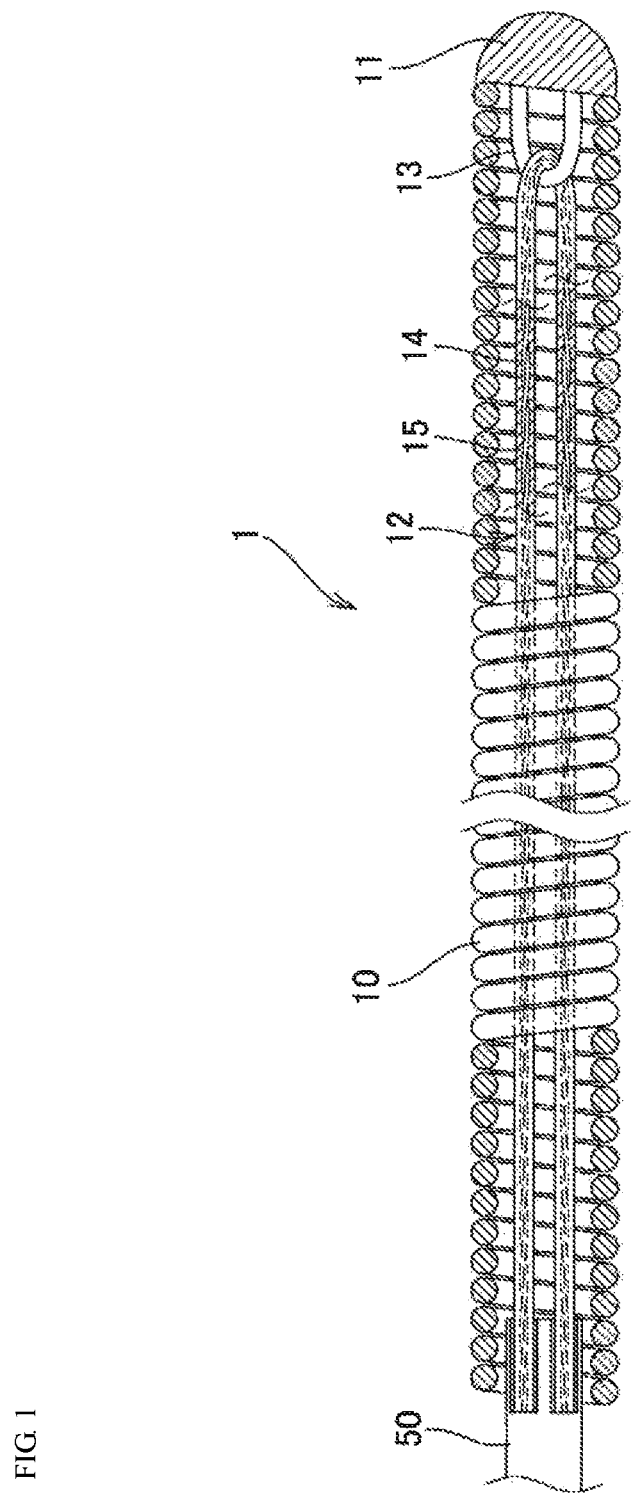
FIG. 1 is a cross-sectional view showing an example of a specific structure of a vascular embolization device 1 according to the present invention.

FIG. 1 is a cross-sectional view showing an example of a specific structure of a vascular embolization device 1 according to the present invention.

The vascular embolization device 1 includes a coil 10 with a primary shape, and a stretch resistant wire 12 provided inside the coil 10.

In this context, the primary shape of the coil refers to the shape formed by winding the wire into the coil.

In the vascular embolization device 1 according to the present invention, the stretch resistant wire 12 is a multilayer strand including at least one core layer 14 and at least one outer layer 15 including one or more resin compositions and a biochemical active material, in which the core layer 14 includes a material with a tensile break strength higher than that of the outer layer 15.

(Coil)

The coil 10 constituting the vascular embolization device 1 is preferably made of an X-ray-impermeable metal wire, such as a wire of any of platinum, gold, tungsten, iridium, palladium, rhodium, indium, iron, nickel, cobalt, chromium, manganese, molybdenum, aluminum, titanium, niobium, silicon, metal phosphide, sulfide mineral, zirconium, copper, stainless steel, and alloys thereof.

The wire used to form the coil 10 preferably has a diameter (wire diameter) of 0.02 mm to 0.12 mm, more preferably 0.03 mm to 0.10 mm, in view of its insertion or placement in blood vessels. The coil 10 preferably has a diameter of 0.1 mm to 1.0 mm, more preferably 0.2 mm to 0.5 mm, in view of its insertion or placement in blood vessels.

In the vascular embolization device, the coil 10 preferably has a length of 1 mm to 1,000 mm, more preferably 1 mm to 500 mm, even more preferably 10 mm to 500 mm.

(Stretch Resistant Wire)

In the present invention, the stretch resistant wire 12 is a multilayer strand including at least one core layer 14 and at least one outer layer 15 including one or more resin compositions, in which the core layer 14 includes a material with a tensile break strength higher than that of the outer layer 15. This brings an advantage such that when the vascular embolization device 1 is placed in the living body, the stretch resistant wire 12 will function to prevent the stretching of coil 10 while releasing the biochemical active material from its outer layer 15.

Figure 2:
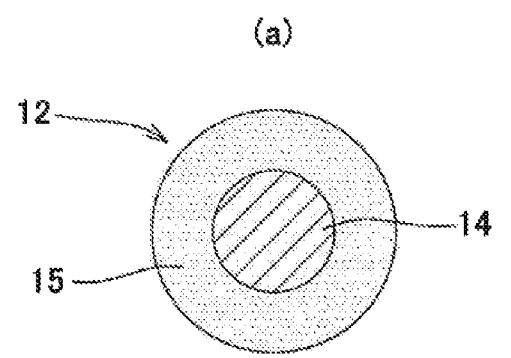
FIG. 2 is an explanatory view showing cross-sections of stretch resistant wires 12 each constituting a vascular embolization device 1 according to the present invention.
Figure 2:
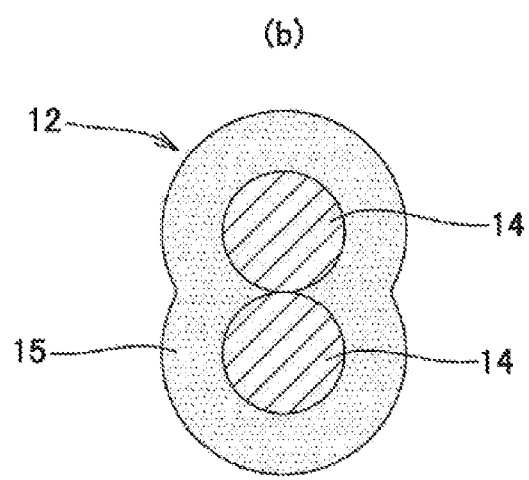

For example, as shown in FIG. 2(a), the stretch resistant wire 12 may include a core layer 14 made of a single wire; and an outer layer 15 that is formed on the surface of the core layer 14 and includes one or more resin compositions. Alternatively, as shown in FIG. 2(b), the stretch resistant wire 12 may include a core layer 14 made of two wires; and an outer layer 15 that is formed on the surface of the core layer 14 and includes one or more resin compositions.

Alternatively, the core layer 14 may include three or more wires as long as they are insertable in the inside of the coil 10. The outer layer 15 may include two or more resins as long as they are insertable in the inside of the coil 10. In addition, two or more outer layers 15 may be provided as long as they are insertable in the inside of the coil 10.

The wire constituting the core layer 14 and the outer layer 15 may also have any diameter and any thickness, respectively, as long as they are insertable in the inside of the coil 10.

The outer layer 15 may also have a multilayer structure including two or more different resin composition layers. In this case, the position of the biochemical active material-containing layer and the content of the biochemical active material may be controlled so that the duration of release of the biochemical active material can be controlled. For example, a resin composition layer including only a resin or having a lower content of the biochemical active material may be formed on the exterior of a biochemical active material-containing layer, so that the biochemical active material can be continuously released at a lower rate over a longer period of time.

Preferably, the stretch resistant wire 12 is folded back at the front end so that the stretch resistant wire 12 is double folded and inserted in the inside of the coil 10. The stretch resistant wire may have any thickness that allows it to be inserted into the inside of the coil 10. In view of the balance between properties such as anti-stretch properties and flexibility, the stretch resistant wire 12 preferably has a thickness of 0.01 mm to 0.10 mm, more preferably 0.01 to 0.06 mm.

In order to prevent the stretching of the coil 10, the stretch resistant wire 12 preferably has a breaking strength of 0.05 N or more per wire, more preferably 0.10 N or more per wire.

The breaking strength can be measured using a tensile tester.

The stretch resistant wire 12, which should be linear as shown in FIG. 1, may be partially or entirely corrugated or spirally-shaped.

The stretch resistant wire 12 corrugated or spirally-shaped partially or entirely can resist straightening (a phenomenon in which when the coil 10 is folded into a compact form and placed in the living body, the stretch resistant wire 12 becomes not long enough so that an end of the coil 10 becomes stiff), so that the coil 10 can be placed in a wider variety of forms depending on the situation in the body. In addition, the corrugated or spirally-shaped stretch resistant wire 12 can have an entire length greater than that of the straight type, so that a larger amount of the biochemical active material can be held inside the coil 10.

Figure 9:
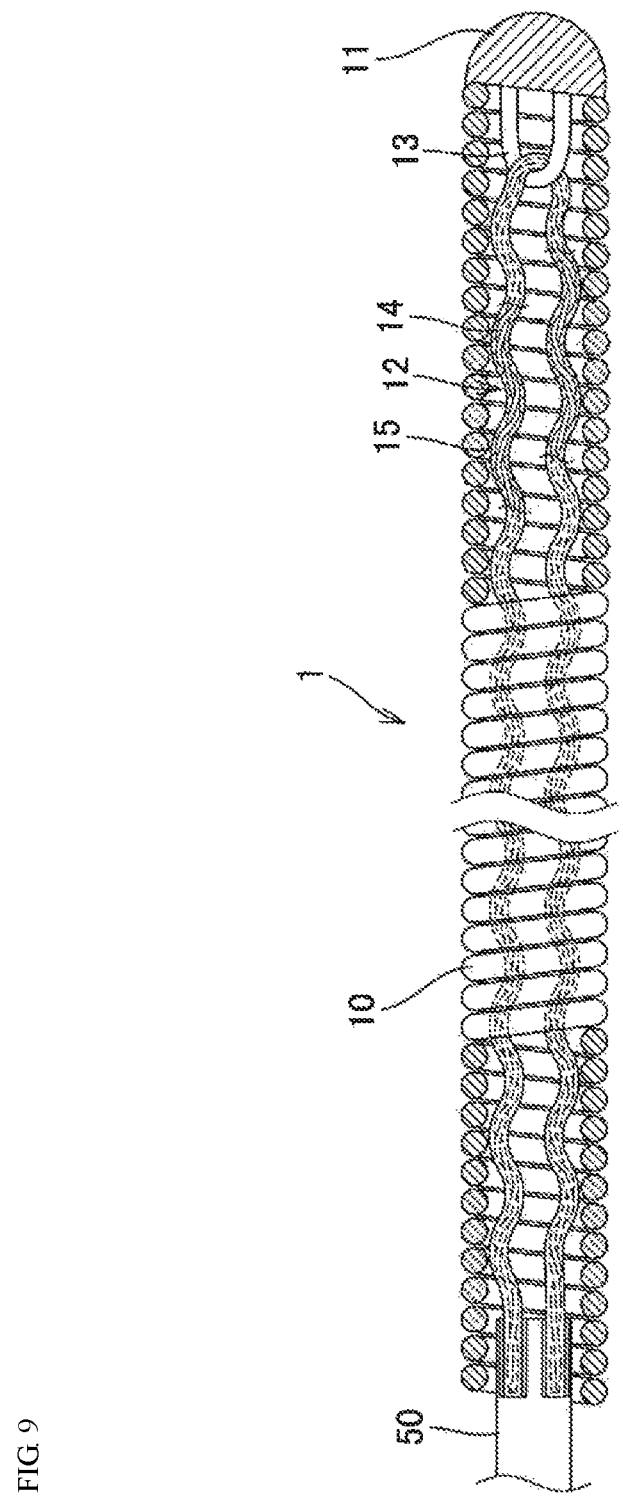
FIG. 9 is a cross-sectional view showing another example of a specific structure of the vascular embolization device 1 according to the present invention.

The corrugated shape may be, for example, a substantially sine wave shape or a substantially square wave shape. For example, as shown in FIG. 9, the stretch resistant wire 12 in the vascular embolization device 1 may be substantially sine wave-shaped over the entire length. The vascular embolization device 1 shown in FIG. 10 has substantially the same features as the vascular embolization device 1 shown in FIG. 9, except that its tip 11 is not provided with a ring part 13 and its connection part 50 is provided with a ring part 23.

The spiral shape may be any helical shape with a size enough to fit in the inside of the coil 10.

The stretch resistant wire 12 prevents excessive stretching of the coil 10 while allowing the coil 10 to deform flexibly. From this point of view, the natural length of the stretch resistant wire 12 is preferably adjusted to be at least 5% longer, more preferably at least 10% longer than the natural length of the coil 10.

In this regard, the natural length of the stretch resistant wire 12 is a longitudinal length of the stretch resistant wire 12. For example, as shown in FIG. 1, it refers to the length of the stretch resistant wire 12 between the ring part 13 and the connection part 50.

In the present invention, the material for use in the core layer 14 may include a metal material or a resin composition. Examples of the material include metals such as platinum, gold, tungsten, tantalum, iridium, palladium, rhodium, indium, iron, nickel, cobalt, chromium, manganese, molybdenum, aluminum, titanium, niobium, silicon, metal phosphide, sulfide mineral, zirconium, copper, stainless steel, and alloys thereof; polymers such as polyethylene, polypropylene, polyethylene terephthalate, polyamide, polyester, polylactic acid, polyglycolic acid, poly(lactic acid-glycolic acid) copolymers, polyhydroxybutyric acid, polyhydroxybutyrate valeric acid, 3-hydroxybutyric acid-3-hydroxyhexanoic acid copolymer polyester; and polymers derived from biodegradable polymers, such as cellulose, polydioxanone, proteins, and vinyl polymers. In view of the anti-stretch function, metals are preferred, and the same metal material as that in the coil is particularly preferred.

Particularly, in view of biocompatibility, gold, platinum, iridium, tungsten, tantalum, titanium, nickel, copper, iron, or an alloy of any combination thereof is preferred when the stretch resistant wire 12 is made of a metal material. For the same reason as in the case of the metal, polyethylene, polypropylene, nylon, polyester, polydioxanone, polytetrafluoroethylene, polyglycolic acid, polylactic acid, silk, or a composite material of any combination thereof is preferred when the stretch resistant wire 12 is made of a resin material.

The resin composition constituting the outer layer 15 of the stretch resistant wire 12 is preferably selected from resin compositions with no adverse effect on the living body.

For example, the resin composition may include a biodegradable resin such as polylactic acid, polyglycolic acid, poly(lactic acid-glycolic acid) copolymer, polycaprolactone, polyhydroxybutyric acid, polyamino acid, cellulose, polyhydroxybutyrate valeric acid, 3-hydroxybutyric acid-3-hydroxyhexanoic acid copolymer polyester, and polyorthoester, or a flexible synthetic polymer material such as an ethylene-vinyl acetate copolymer, a styrene-isobutylene-styrene block copolymer, a styrene-ethylene-propylene-styrene block copolymer, a styrene-ethylene-butadiene-styrene block copolymer, or a styrene-ethylene-ethylene-propylene-styrene block copolymer.

Among these resins, a biodegradable resin and an ethylene-vinyl acetate copolymer are preferred, and a poly(lactic acid-glycolic acid) copolymer and an ethylene-vinyl acetate copolymer are more preferred, because they can surely hold a necessary and sufficient amount of the biochemical active material and can properly release the biochemical active material upon contact with blood.

When the resin composition includes the biodegradable resin, the resin preferably has a weight average molecular weight of 1,000 to 200,000, more preferably 2,500 to 100,000, even more preferably 5,000 to 24,000, so that the resin can offer a good balance of mechanical properties and solubility in solvents.

When the resin composition includes the ethylene-vinyl acetate copolymer, the copolymer preferably has a vinyl acetate unit content of 10% by weight to 50% by weight, more preferably 30% by weight to 50% by weight, in view of solubility in organic solvents.

The biochemical active material, which is held in the resin composition and constitutes the outer layer 15 of the stretch resistant wire 12, may be an organization promoter, a blood coagulation accelerator, an anticancer drug, or any other drug according to the desired purpose.

For example, a resin composition containing an organization promoter may be used to form the stretch resistant wire 12, so that the resulting vascular embolization device 1 can promote the formation of biological tissues when placed in the aneurysm to be embolized. Such an organization promoter is preferably any of statins such as simvastatin, pravastatin, atorvastatin, pitavastatin, fluvastatin, lovastatin, and rosuvastatin. In particular, one or any combination of simvastatin, pravastatin, atorvastatin, and pitavastatin is preferably used.

A resin composition containing a blood coagulation accelerator may also be used to form the stretch resistant wire 12, so that vascular closure can be accelerated in the blood vessel where the resulting vascular embolization device 1 is used for embolization. Examples of such a blood coagulation accelerator include coagulation accelerators such as phytonadione, protamine sulfate, hemocoagulase, and menatetrenone, external hemostatics such as sodium alginate, gelatin, and oxidized cellulose, blood coagulation factor preparations such as eptacog alfa, octocog alfa, turoctocog alfa, desmopressin acetate hydrate, thrombin, and rurioctocog alfa, sclerosants for esophageal varices, such as oleic acid monoethanolamine and polidocanol, antiplasmin agents such as tranexamic acid, and capillary stabilizers such as ascorbic acid, carbazochrome, phytonadione, carbazochrome sodium sulfonate hydrate, and adrenochrome monoaminoguanidine mesilate.

A resin composition containing an anticancer drug may also be used to form the stretch resistant wire 12, which makes it possible to accelerate degeneration and elimination of cancer tissues around the blood vessel where the resulting vascular embolization device 1 is used for embolization. Examples of such an anticancer drug include alkaloids such as paclitaxel, cytochalasin, docetaxel, vincristine, vinblastine, vinorelbine, etoposide, teniposide, misplatin, vindesine, and irinotecan; antibiotics such as mitomycin, adriamycin, doxorubicin, actinomycin, daunorubicin, idarubicin, mitoxantrone, bleomycin, plicamycin, aclarubicin, pirarubicin, epirubicin, peplomycin, neocarzinostatin, and zinostatin stimalamer; alkylating agents such as nitrogen mustard, mechlorethamine, cyclophosphamide, melphalan, chlorambucil, ethyleneimine, thiotepa, methyl melanin, busulfan, carmustine, streptozocin, dacarbazine, procarbazine, carboquone, nimustine, ranimustine, mitobronitol, and temozolomide; antimetabolites such as methotrexate, fluorouracil, floxuridine, cytarabine, mercaptopurine, thioguanine, mentostatin, chlorodeoxyadenosine, hydroxycarbamide, Starasid ocfosphate, enocitabine, fludarabine, gemcitabine, doxifluridine, Tegafur, Tegafur uracil, Levofolinate, carmofur, methotrexate, TS One (registered trademark), and capecitabine; platinum-based agents such as cisplatin, carboplatin, and nedaplatin; hormone drugs such as leuprorelin, goserelin, medroxyprogesterone, tamoxifen, toremifene citrate, fadrozole, estramustine sodium phosphate ester, flutamide, and bicalutamide; retinoids such as tretinoin; and other drugs such as imatinib, dasatinib, nilotinib, gefitinib, folinate, mozavaptane, sunitinib, sorafenib, axitinib, lapatinib, azathioprine, cyclosporine, tacrolimus, sirolimus, zotarolimus, everolimus, Biolimus A9, mycophenolate mofetil, mizoribine, calcipotriol, gusperimus, muromonab-CD3, thalidomide, lenalidomide, bicalutamide, aceglatone, octreotide, pentostatin, sobuzoxane, porfimer sodium, tranilast, sodium aurothiomalate, penicillamine, lobenzarit, bucillamine, losartan potassium, candesartan cilexetil, valsartan, lisinopril, captopril, cilazapril, enalapril, temocapril hydrochloride, quinapril hydrochloride, trandolapril, delapril hydrochloride, perindopril erbumine, nifedipine, nilvadipine, efonidipine hydrochloride, felodipine, and colchicine.

The content of the biochemical active material in the outer layer 15 of the stretch resistant wire 12 is preferably from 1 part by weight to 99 parts by weight, more preferably from 1 part by weight to 60 parts by weight, even more preferably from 1 part by weight to 50 parts by weigh, based on 100 parts by weight of the resin composition constituting the outer layer 15.

In the present invention, the "stretch resistant wire containing a biochemical active material" is intended to include (1) a stretch resistant wire having an outer layer 15 including a resin composition containing a biochemical active material uniformly dissolved or dispersed therein, (2) a stretch resistant wire having an outer layer including a resin composition, and a biochemical active material being localized at and near the surface of the outer layer (e.g., a stretch resistant wire containing a biochemical active material applied to the surface of the resin composition), and (3) a stretch resistant wire containing a resin composition and a biochemical active material localized inside the resin composition (e.g., a stretch resistant wire containing a biochemical active material (inner part) covered with a resin film (outer part).

Figure 3:
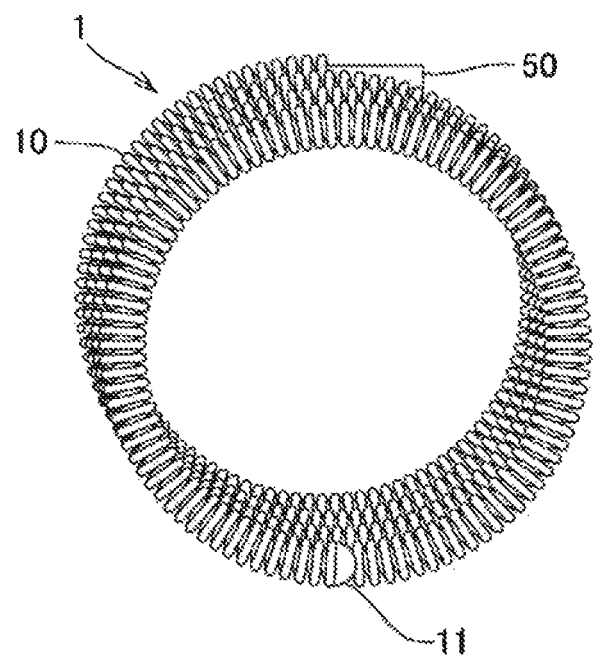
FIG. 3 is an explanatory view showing an example of a secondary shape formed by winding, into a coil, the vascular embolization device 1 according to the present invention.

FIG. 1 shows the vascular embolization device 1 in a primary form extending linearly. For example, when moved in a catheter, the vascular embolization device 1 takes this form. When not restrained by a catheter tube wall or other structure, the vascular embolization device 1 takes the form of a secondary coil, in which the coil 10 is further wound as shown in FIG. 3. A connection part 50 including a resin wire for coil separation is connected and fixed to the rear end of the coil 10.

In this regard, the diameter of the secondary coil, which is appropriately selected according to the inner diameter of the target site (e.g., aneurysm), is preferably from 1 mm to 40 mm, more preferably from 1.5 mm to 20 mm.

(Tip)

The stretch resistant wire should be fixed at the front end of the vascular embolization device 1 of the present invention. For this purpose, a tip 11 is preferably provided at the front end of the coil 10.

When the coil 10 is placed at the target site in the blood vessel, the coil 10 should be prevented from stretching. For this purpose, the stretch resistant wire 12 inserted in the inside of the primary-shaped coil 10 is preferably fixed at at least two sites including the rear end of the coil 10 and the tip 11 fixed at the front end of the coil 10.

As shown in FIG. 1, the tip 11 has a ring part 13 that is provided on the inside side of the coil 10 to fix the stretch resistant wire 12.

In addition, the outer surface of the tip 11 is preferably smooth sphere- or hemisphere-shaped in order to prevent any damage to the target sites in the blood vessel.

The tip 11 may be formed by melting and shaping a front end portion of the wire of the coil 10 into a desired shape. Alternatively, a tip-forming member separate from the coil 10 may be fixed to the coil 10 with an adhesive or by heat welding to form the tip 11.

Figure 10:
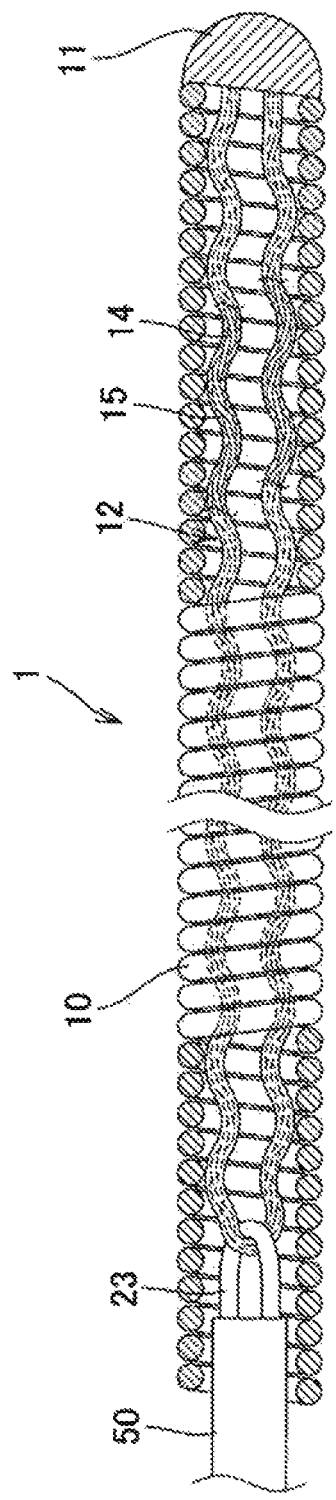
FIG. 10 is a cross-sectional view showing a further example of a specific structure of the vascular embolization device 1 according to the present invention.

Alternatively, as shown in FIG. 10, the stretch resistant wire 12 may be fixed to the tip 11 without the ring 13 in the vascular embolization device 1 of the present invention. In this case, a ring part 23 may be provided on the connection part 50 at the rear end of the coil 10, and the stretch resistant wire may be hooked on the ring 23.

In the present invention, both ring parts 13 and 23 may also be provided (not shown), for example, when the spirally-shaped stretch resistant wire 12 is inserted in the inside of the coil 10.

(Pushing Means)

Figure 4:
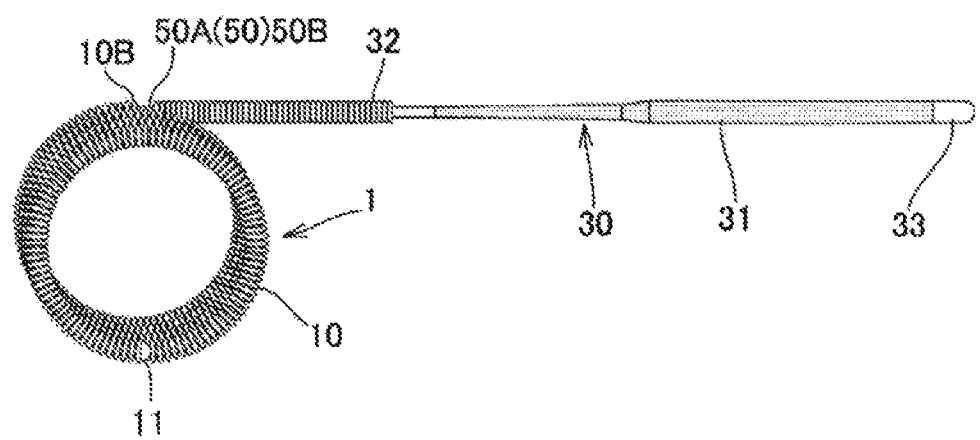
FIG. 4 is an explanatory view showing the connection of pushing means 30 to the vascular embolization device 1 according to the present invention.

As shown in FIG. 4, the rear end of the coil 10 is attached to pushing means 30 with a connection part 50 interposed therebetween.

As shown in FIG. 1, the coil 10 and the stretch resistant wire 12 are fixed to the connection part 50.

In this regard, the stretch resistant wire 12 may be fixed to any position of the connection part 50, such as the surface or interior.

In addition, the connection part 50 is so designed as to detachably connect the vascular embolization device 1.

Various methods may be used to detach the vascular embolization device 1. Typical detaching methods include, for example, detachment by thermally dissolving a resin wire of the connection part 50, detachment by electrolysis of a metal wire of the connection part 50, detachment by water pressure pushing, and detachment by mechanical unlocking. Among them, the method of detaching the coil 10 by dissolving the wire of the connection part is preferably used. Examples of the resin for forming the resin wire for coil separation include hydrophilic resins of synthetic polymers, including polyvinyl alcohol-based polymers such as polyvinyl alcohol (PVA), cross-linked PVA polymers, elastomers produced by freezing and thawing water absorption PVA gel, and ethylene-vinyl alcohol copolymers.

Among them, polyvinyl alcohol-based polymers are preferred because they can swell upon being in contact with water while maintaining a constant strength and can dissolve upon being heated at such a level as not to damage the living body.

FIG. 4 shows that pushing means 30 as an introducer is connected to the vascular embolization device 1 of the present invention (the vascular embolization device 1 with the features shown in FIG. 1). The pushing means 30 shown in FIG. 4 includes a wire portion 31 and a radiopaque distal portion 32 extending therefrom, in which the wire portion 31 includes a core wire and a resin coating layer formed on the outer surface of the core wire. The radiopaque distal portion 32 is connected and fixed to the rear end 50B of the resin wire constituting the connection part 50 fixed to the rear end 10B of the coil 10, so that the pushing means 30 is connected to the vascular embolization device 1. In this case, the rear end 10B of the coil 10 and the front end 50A of the resin wire constituting the connection part 50 for coil separation may be fixed to each other by any means, such as bonding with an adhesive, welding, connection by physical force, or other fixing means, and the radiopaque distal portion 32 of the pushing means 30 and the rear end 50B of the resin wire constituting the connection part 50 may also be fixed to each other by any means, such as bonding with an adhesive, welding, connection by physical force, or other fixing means.

The pushing means 30 preferably has an outer diameter of 0.1 mm to 2.0 mm. The pushing means 30 preferably has a length of 0.1 m to 2.0 m.

The core wire constituting the pushing means 30 is preferably a wire made of an electrically-conductive material such as stainless steel.

The resin coating layer in the wire portion 31 of the pushing means 30 can be formed by, for example, applying a fluororesin or a hydrophilic resin to the outer surface of the core wire. The resin coating layer made of a fluororesin or a hydrophilic resin is advantageous in that it can reduce the surface friction coefficient.

At the outer end of the wire portion 31, the core wire is exposed to form a terminal portion 33, through which electric power can be supplied to the core wire via an appropriate conductive member such as an electric connector, plugs, or clips. The terminal portion 33 with a length of about 1 cm to about 3 cm is long enough.

The radiopaque distal portion 32 of the pushing means 30 has a secondary form in which a winding wire is further wound into a coil on the outer surface of the core wire. A wire made of a metal such as platinum, silver, gold, tungsten, or stainless steel may be used for the winding wire that forms the radiopaque distal portion 32.

The vascular embolization device 1 of the present invention to which the pushing means 30 is connected as shown in FIG. 4 is introduced through any appropriate catheter to the target site in the living body.

Figure 5:
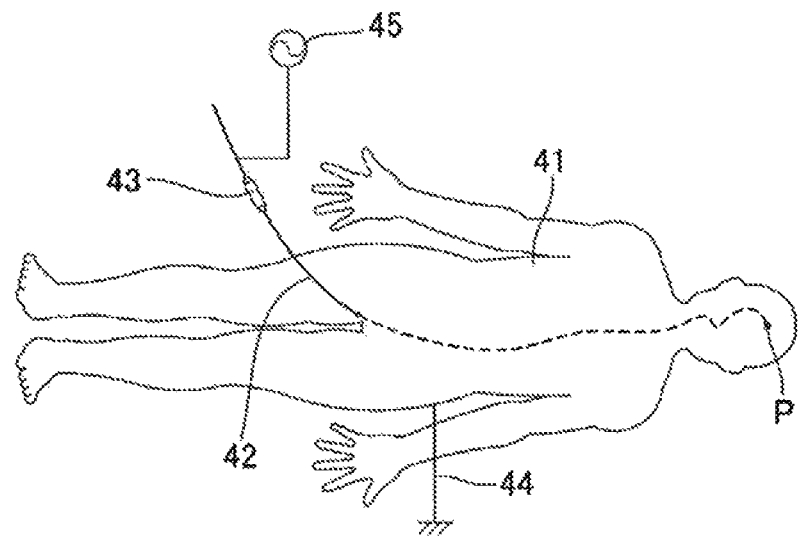
FIG. 5 is an explanatory view showing how to use the vascular embolization device 1 according to the present invention in the human body.

Specifically, as shown in FIG. 5, a catheter 42 is first inserted in such a manner that its front end opening reaches a target site P in the living body 41, and the vascular embolization device 1 as a front part is then inserted from a hand operation unit 43 into the catheter 42. Thus, the vascular embolization device 1 is moved in a linearly extended form through the catheter 42 while being pushed by the pushing means 30 and pushed out to the target site P from the front end opening of the catheter 42. When the connection part 50 reaches the front end opening of the catheter 42, an earth electrode 44 is attached to an appropriate skin surface of the living body 41, and, for example, a monopolar high-frequency current is supplied to the pushing means 30 from a high-frequency power supply 45 connected to the terminal portion 33 of the pushing means 30.

As a result, the high-frequency current generates heat to melt and cut off the rear end 50B of the resin wire constituting the connection part 50 between the vascular embolization device 1 and the pushing means 30, so that the vascular embolization device 1 is separated from the pushing means 30 and successfully placed at the target site P.

Therefore, when a resin with a melting point of 100° C. or less is selected as a component of the resin wire constituting the connection part 50, the rear end 50B of the resin wire can be cut off in a short time by heating during high-frequency current supply.

Specifically, the resin wire constituting the connection part 50 may be made of a hydrophilic resin including a polyvinyl alcohol based polymer. In this case, the rear end 50B of the resin wire can be melted and cut off in a very short time of at most 3 seconds by supplying a high-frequency current.

This makes it possible to significantly reduce the burden on not only the operator but also the living body undergoing the operation and also makes it possible to significantly reduce the possibility of occurrence of unexpected events on the living body during the placement operation.

The vascular embolization device having the features described above can provide a good therapeutic effect by having good coil delivery performance, a good embolization function, and a drug delivery function.

Hereinafter, a method for producing the vascular embolization device of the present invention will be described, which, however, is not intended to limit the present invention.

A method for producing the vascular embolization device of the present invention includes the following three steps (a), (b), and (c).

(a) coating the surface of a core layer-forming material with a solution containing a biochemical active material and a resin composition;

(b) drying the solution to form an outer layer containing one or more resin compositions so that a stretch resistant wire is formed; and (c) inserting the stretch resistant wire into the inside of a coil to form a vascular embolization device.

The details of the steps (a), (b), and (c) may be appropriately controlled according to the features of the vascular embolization device.

For example, the vascular embolization device 1 shown in FIGS. 1 and 4 can be produced by the following steps.

- (a1) A twisted strand forming step including stranding wires to form a twisted strand as a core 14
- (a2) A coating step including coating the surface of the twisted strand with a solution containing a biochemical active material and a resin composition
- (b) A drying step including drying the solution to form a biochemical active material-containing layer (outer layer 15) on the core 14
- (c) An assembling step including inserting, into the inside of a coil 10, a stretch resistant wire 12 having the biochemical active material-containing layer
- (d) A tip forming step including forming a front end tip 11 at the front end of the coil 10
- (e) A bonding step including bonding a resin wire (connection part 50) for coil separation to the base end of the coil 10 and to the front end of the wire of pushing means 30
- (f) A trimming step including removing, by cutting, an excess part of the stretch resistant wire 12 protruding from the base end of the coil 10

Alternatively, the method may include, instead of the steps (a1) and (a2),

- (a3) a corrugated or spirally-shaped wire forming step including corrugating or spirally-shaping a wire to form a core 14, and
- (a4) a coating step including coating the surface of the corrugated or spirally-shaped wire with a solution containing a biochemical active material and a resin composition, which may be followed by the steps (b), (c), (d), (e), and (f) mentioned above.

Hereinafter, each step will be described in detail.

(a1) Twisted Strand Forming Step

In a stranding machine, wires with a desired diameter are wound on two bobbins. The wires for forming the core 14 of the stretch resistant wire 12 are drawn from the two bobbins being rotated and stranded to form a twisted strand, which is taken up on another bobbin.

(a2) Coating Step Using an X stage and a dispenser, a die, a spray, or other means, the surface of the twisted strand placed linearly is coated with a solution containing a biochemical active material and a resin composition.

(b) Drying Step

In a vacuum heating oven, the solution is dried under reduced pressure at 40 to 80° C. for 1 to 24 hours, so that a corrugated stretch resistant wire 12 having a biochemical active material-containing layer (outer layer 15) is obtained.

(c) Assembling Step

Under microscopic observation, the stretch resistant wire 12 having the biochemical active material-containing layer is inserted into the inside of the coil 10.

(d1) Tip Forming Step

Using a YAG laser irradiation device, a tip 11 is formed by irradiating the coil 10 with laser light focused on the front end of the coil 10.

In addition, a ring part 13 is formed on the inside side of the coil 10. The stretch resistant wire 12 is inserted into the ring part 13 and then folded back at the ring part 13.

(e1) Bonding Step

Under microscopic observation, a resin wire 50 for coil separation is inserted into the base end of the coil 10 using a dispenser, and then they are bonded together with an instantaneous adhesive. At the same time, the stretch resistant wire 12 is also bonded to the surface of the resin wire 50 for coil separation. After the adhesive is cured, the resin wire 50 for coil separation, which extends from the coil 10, is similarly bonded to the front end of the wire of the pushing means 30 with an instantaneous adhesive.

(f) Trimming Step

Under microscopic observation, an excess part of the stretch resistant wire 12 protruding from the base end of the coil 10 is removed by cutting.

(a3) Corrugated or Spirally-Shaped Wire Forming Step

A wire for forming the core 14 of the stretch resistant wire 12 is corrugated by being sandwiched between corrugated dies and then taken up on a bobbin.

Alternatively, a wire for forming the core 14 of the stretch resistant wire 12 may be wound on the surface of a linear or curved core material to form a corrugated or spirally-shaped wire.

(a4) Coating Step

Using an X stage and a dispenser, a die, a spray, or other means, the surface of the corrugated wire placed linearly is coated with a solution containing a biochemical active material and a resin composition.

(b) Drying Step

In a vacuum heating oven, the solution is dried under reduced pressure at 40 to 80° C. for 1 to 24 hours, so that a corrugated stretch resistant wire 12 having a biochemical active material-containing layer (outer layer 15) is obtained.

(c) Assembling Step

The corrugated stretch resistant wire 12 having the biochemical active material-containing layer is inserted into the inside of the coil 10.

(d2) Tip Forming Step

Under microscopic observation, a predetermined length portion of the corrugated stretch resistant wire 12 having the biochemical active material-containing layer is allowed to protrude from the front end of the coil 10. The predetermined length portion of the stretch resistant wire 12 is coated with an adhesive and bonded to the coil 10 to form a tip 11.

(e2) Bonding Step

Under microscopic observation, a resin wire 50 for coil separation is inserted into the base end of the coil 10 using a dispenser, and then they are bonded together with an adhesive. After the adhesive is cured, the resin wire 50 for coil separation, which extends from the coil 10, is similarly bonded to the front end of the wire of the pushing means 30 with an instantaneous adhesive.

The stranding machine, X stage, dispenser, dies, spray, vacuum heating oven, microscope, YAG laser irradiation device, instantaneous adhesive, and other means are not particularly limited, but may be of any type useful for medical device production.

EXAMPLES

Hereinafter, the present invention will be more specifically described with reference to examples. It will be understood that the examples below are not intended to limit the present invention.

Example 1

A twisted strand was formed, which was composed of two wires each containing 92% platinum and 8% tungsten with a diameter of 0.01 mm. At room temperature, the surface of the twisted strand was then coated with a solution obtained by dissolving 0.30 g of atorvastatin (AV) and 0.30 g of poly(50% lactic acid-50% glycolic acid) copolymer (PLGA)

(weight average molecular weight: 10,000, melt viscosity: 0.122 to 0.143 g/dl) in 1.8 mL of acetone. The acetone was then evaporated to dryness by heating under reduced pressure, so that a stretch resistant wire A (atorvastatin content: 0.56 μg/mm) was obtained, which had a resin composition outer layer carrying the drug.

The side surface of the prepared stretch resistant wire A was observed with a digital microscope. As a result, it was observed that an about 0.01 mm-thick drug-containing layer (outermost layer) was formed on the surface of the base wire (core layer). The breaking strength of one piece of the stretch resistant wire A was measured using a tensile tester, and the obtained measurement was to be 0.5 N.

The stretch resistant wire A was inserted in the inside of a metal coil with an element wire diameter of 0.045 mm, a primary coil diameter of 0.30 mm, and a secondary coil diameter of 4 mm. The product was subjected to the steps (c), (d), (e), and (f) described above, so that a vascular embolization device 1 having the structure shown in FIGS. 1 and 4 was obtained.

Figure 6:
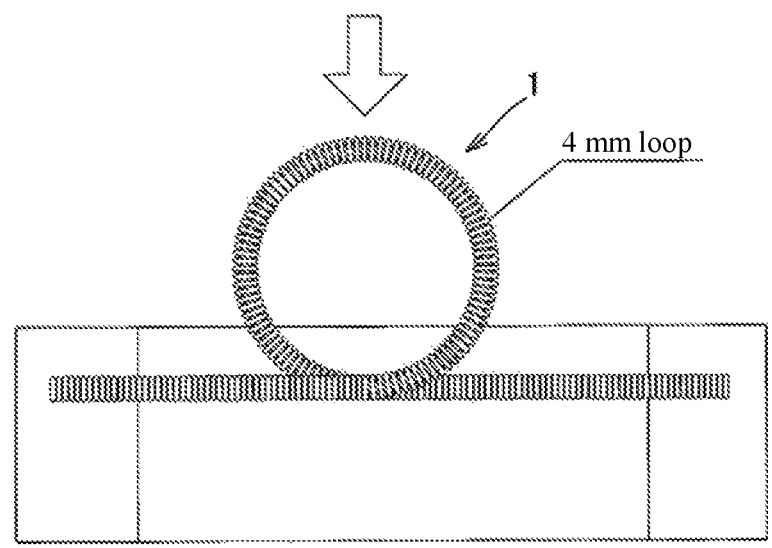
FIG. 6 is an explanatory view showing a method for measuring the coil flexibility of the vascular embolization devices prepared in Examples 1 and 2 and Comparative Example 1.
Figure 7:
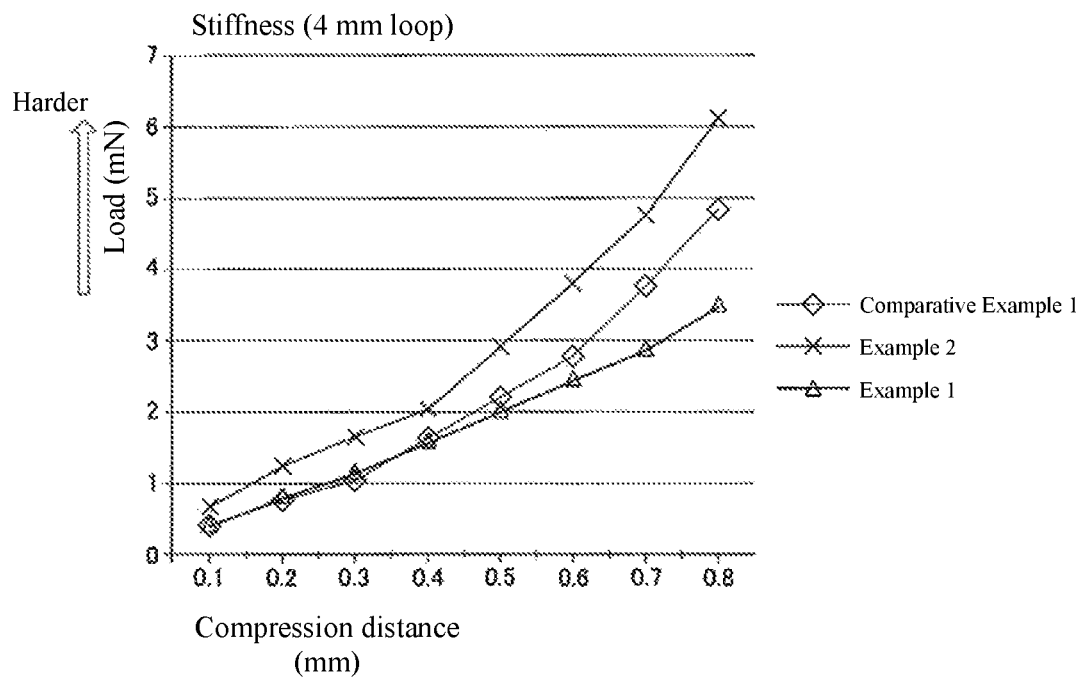
FIG. 7 is a graph showing the results of measurement of the coil flexibility of the vascular embolization devices prepared in Examples 1 and 2 and Comparative Example 1.

The resulting vascular embolization device 1 was evaluated for coil flexibility. In the evaluation, the vascular embolization device 1 was fixed in the form of a loop with a diameter of 4 mm, which was equal to the secondary diameter of the coil to be tested, and the load required to compress the coil loop by a predetermined distance from the top was measured (FIG. 6). FIG. 7 shows the results.

Example 2

A vascular embolization device having a stretch resistant wire was prepared and evaluated for coil flexibility using the same method as in Example 1, except that the atorvastatin content was changed to 1.32 μg/mm. FIG. 7 shows the results.

Comparative Example 1

An embolization coil was prepared and evaluated for coil flexibility using the same method as in Example 1, except that the outer layer including the resin composition that carries the drug was not formed. FIG. 7 shows the results.

The coil flexibility is compared at the same compression distance. A higher compression load means a higher coil stiffness and therefore a lower flexibility.

The measurement results of Examples 1 and 2 and Comparative Example 1 in FIG. 7 show that the vascular embolization devices of Examples 1 and 2 have a similar degree of flexibility to that of the embolization coil of Comparative Example 1 with neither the drug nor the resin and thus can be safely placed at a desired target site in the blood vessel. The vascular embolization devices of Examples 1 and 2 also have a high embolization effect because they contain atorvastatin in a biodegradable resin layer provided on the surface of the stretch resistant wire disposed inside the coil so that atorvastatin can be slowly released from the biodegradable resin layer when they are placed in blood vessels.

Test Example

The vascular embolization device prepared in Example 1, the embolization coil prepared in Comparative Example 1, and a common commercially available embolization coil (Target™ HELICAL ULTRA, Cat. No. 543408) were evaluated for flexibility in the same manner as described above.

Figure 8:
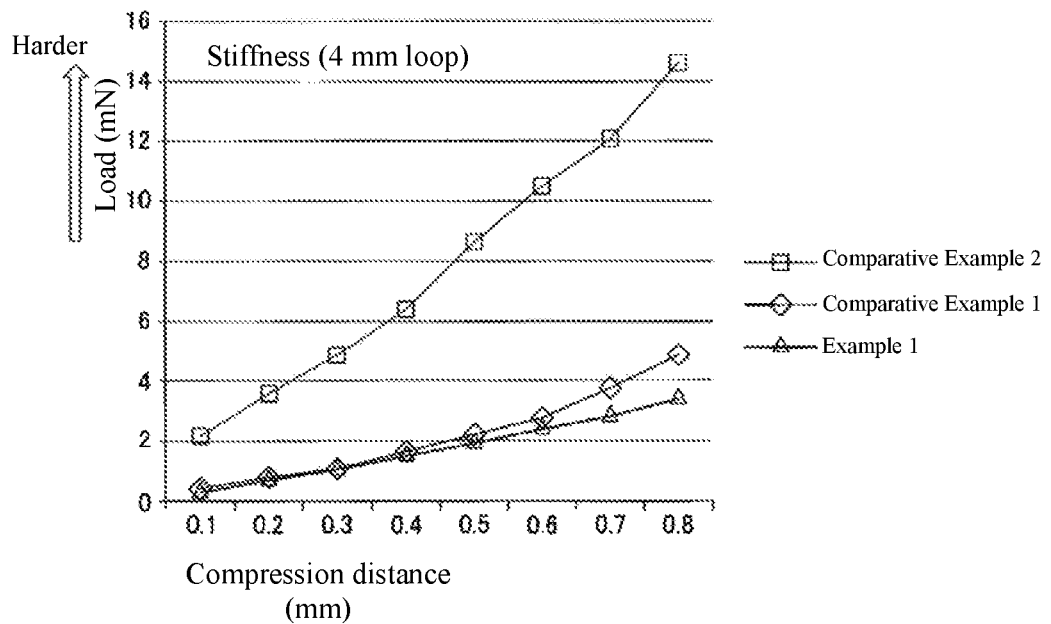
FIG. 8 is a graph showing the results of measurement of the coil flexibility of a commercially available product and the vascular embolization devices prepared in Example 2 and Comparative Example 1.

FIG. 8 shows the results. Note that in the drawing, the commercially available product is expressed as "Comparative Example 2."

The results in FIG. 8 show that the vascular embolization device prepared in Example 1 is more flexible than the commercially available embolization coil and thus can be safer in placement and other operation procedures.

It is also apparent that the vascular embolization device prepared in Example 1 has substantially the same degree of flexibility as that of the embolization coil of Comparative Example 1 with no drug-resin composition coating.

Example 3

A polypropylene (PP) wire with a diameter of 0.03 mm was corrugated with a period of 0.3 mm and an amplitude of 0.05 mm. A solution was obtained by dissolving, in tetrahydrofuran (THF), atorvastatin (AV) and an ethylene-vinyl acetate copolymer (EVA) (vinyl acetate (VA) content: 40% by weight, EVA: 28% by weight, average molecular weight: 180,000) in a ratio of 4:6. The solution was applied to the surface of the corrugated PP wire at room temperature by spraying. The THF was evaporated to dryness by heating under reduced pressure, so that a corrugated stretch resistant wire B (atorvastatin content 20.0 μg/cm) was obtained, which had a resin composition outer layer carrying the drug.

The side surface of the prepared stretch resistant wire B was observed with a digital microscope. As a result, it was observed that an about 0.015 mm-thick drug-containing layer (outer layer) was formed on the surface of the base wire (core layer).

The breaking strength of one piece of the stretch resistant wire B was measured using a tensile tester, and the obtained measurement was 0.4 N.

The stretch resistant wire B was inserted in the inside of a metal coil with an element wire diameter of 0.035 mm, a primary coil diameter of 0.25 mm, and a secondary coil diameter of 2 mm. After the step (c), the product was subjected to (g) a coil front end fixing step, (h) a front end bonding step, (i) a coil base end fixing step, and the step (e) sequentially, so that a vascular embolization device having the structure shown in FIG. 9 was obtained. In this case, 9-0PP sutures were used for the head ring part provided on the inside of the coil.

The vascular embolization devices prepared in Examples 1 and 3 have substantially the same coil length. Here, the natural length of the stretch resistant wire B in the inside of the coil is 10 cm, whereas the natural length of the stretch resistant wire A in the vascular embolization device of Example 1 is 11.2 cm. Thus, the stretch resistant wire B is at least 10% longer than the stretch resistant wire A.

This means that the content of the drug in the stretch resistant wire of the vascular embolization device of Example 3 is higher than that in the stretch resistant wire of the vascular embolization device of Example 1.

The vascular embolization device prepared in Example 3 was also examined for coil flexibility by the method described above in the section "Test Example." As a result, the vascular embolization device of Example 3 was found to have substantially the same degree of flexibility as that of the vascular embolization device of Example 1.

Example 4

A solution of a mixture of AV and EVA (solvent THF) was applied to a PP wire in Example 3. Subsequently, only a THF solution of the same EVA was applied to the PP wire at room temperature by spraying. The THF was then evaporated to dryness by heating under reduced pressure, so that a corrugated stretch resistant wire C (atorvastatin content 20.0 μg/cm) was obtained, which had a resin composition outer layer carrying the drug.

The side surface of the prepared stretch resistant wire C was observed with a digital microscope. As a result, it was observed that an about 0.005 mm-thick EVA layer was formed on the surface of the stretch resistant wire B.

Figure 11:
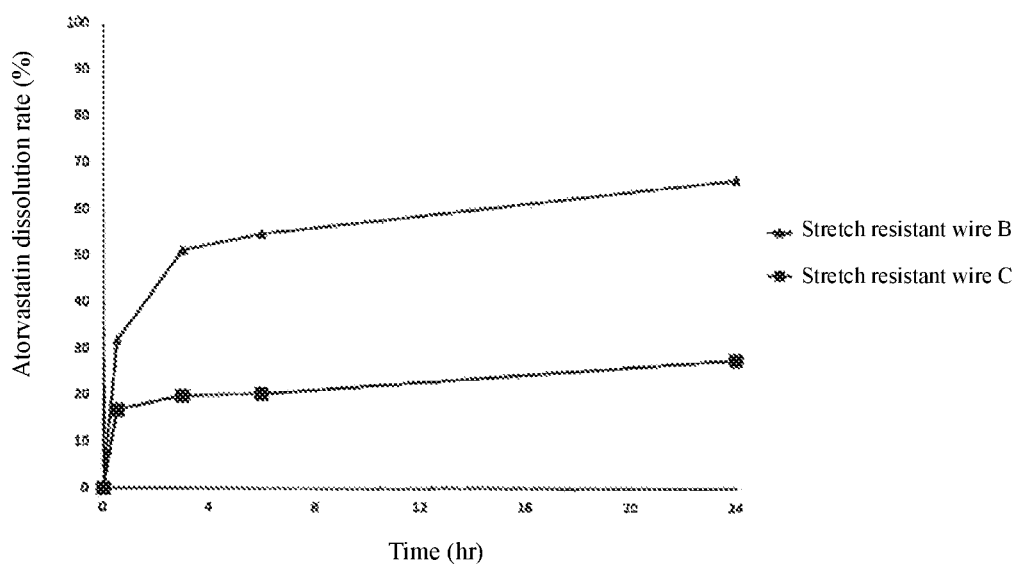
FIG. 11 is a graph showing the results of a dissolution test performed in Example 4 where stretch resistant wires B and C carrying a drug are each immersed in a phosphate buffer and the content of the drug in the PBS is quantified at regular time intervals.

The drug-carrying stretch resistant wires B and C were each immersed in a phosphate buffer solution (PBS) at 37° C. and subjected to a dissolution test in which the content of the drug in the PBS was quantified at regular time intervals. The results in FIG. 11 were obtained showing that the stretch resistant wire C having the EVA layer as the outermost layer has a drug release rate lower than that of the stretch resistant wire B.

REFERENCE SIGNS LIST

10 Coil
11 Tip
12 Stretch resistant wire
13 Ring part
14 Core layer
15 Outer layer
23 Ring part
30 Pushing means
31 Wire portion
32 Radiopaque distal portion
33 Terminal portion
41 Living body
42 Catheter
43 Hand operation unit
44 Earth electrode
45 High-frequency power supply
50 Connection part

The invention claimed is:

1. A vascular embolization device comprising:
a coil with a primary shape; and
a stretch resistant wire provided in an inside of the coil, wherein
the stretch resistant wire comprises at least one core as an innermost layer and an outer layer,
the at least one core comprises a material with a tensile break strength higher than a tensile break strength of the outer layer,
the outer layer of the stretch resistant wire has a multilayer structure including two or more layers, and at least one layer of the two or more layers comprises a mixture of an ethylene-vinyl acetate copolymer and a biochemical active material,
the at least one core does not contain a biochemical active material,
the stretch resistant wire has a break strength of at least 0.05 N per wire, and
the at least one core of the stretch resistant wire is made of a resin.

2. The vascular embolization device according to claim 1, wherein the coil is wound into a predetermined shape as a secondary shape, such that the secondary shape of the coil is different from the primary shape.

3. The vascular embolization device according to claim 1 or 2, wherein the ethylene-vinyl acetate copolymer has a vinyl acetate unit content of 10 to 50% by weight.

4. The vascular embolization device according to claim 1, wherein the stretch resistant wire has a thickness of 0.01 to 0.10 mm.

5. The vascular embolization device according to claim 1, wherein the stretch resistant wire is corrugated or spirally shaped.

6. The vascular embolization device according to claim 1, wherein the stretch resistant wire has a natural length at least 5% longer than a natural length of the coil.

7. The vascular embolization device according to claim 1, wherein the at least one core of the stretch resistant wire is made of a metal.

8. The vascular embolization device according to claim 7, wherein the metal is selected from the group consisting of gold, platinum, iridium, tungsten, tantalum, titanium, nickel, copper, iron, and an alloy of any combination thereof.

9. The vascular embolization device according to claim 1, wherein the at least one core of the stretch resistant wire is made of a resin selected from the group consisting of polyethylene, polypropylene, nylon, polyester, polydioxanone, polytetrafluoroethylene, polyglycolic acid, polylactic acid, silk, and a composite material of any combination thereof.

10. The vascular embolization device according to claim 1, wherein the at least one layer of the two or more layers comprising the ethylene-vinyl acetate copolymer and the biochemical active material is an outermost layer of the multilayer structure of the outer layer.

11. The vascular embolization device according to claim 1, wherein the biochemical active material comprises a statin.

12. The vascular embolization device according to claim 11, wherein the statin is at least one type selected from the group consisting of simvastatin, pravastatin, atorvastatin, pitavastatin, and any combination thereof.

13. The vascular embolization device according to claim 1, wherein the at least one layer of the two or more layers contains 1 part by weight to 99 parts by weight of the biochemical active material based on 100 parts by weight of the total amount of the biochemical active material and the ethylene-vinyl acetate copolymer.

14. The vascular embolization device according to claim 1, wherein the at least one layer of the two or more layers contains 1 part by weight to 60 parts by weight of the biochemical active material based on 100 parts by weight of the total amount of the biochemical active material and the ethylene-vinyl acetate copolymer.

15. The vascular embolization device according to claim 1, wherein
the stretch resistant wire is disposed in the inside of the coil such that the stretch resistant wire extends from a proximal side of the coil to a distal side of the coil.

16. A method for producing the vascular embolization device according to claim 1, the method comprising the steps of:
(a) coating a surface of a material forming the at least one core with a solution containing the biochemical active material and the ethylene-vinyl acetate copolymer;
(b) drying the solution to form the outer layer containing the ethylene-vinyl acetate copolymer and the biochemical active material, thereby preparing the stretch resistant wire; and
(c) inserting the stretch resistant wire into the inside of the coil to form the vascular embolization device.

* * * * *